US012626788B2

(12) United States Patent
Pai et al.

(10) Patent No.: US 12,626,788 B2
(45) Date of Patent: May 12, 2026

(54) INCREMENTALLY TRAINING A KNOWLEDGE GRAPH EMBEDDING MODEL FROM BIOMEDICAL KNOWLEDGE GRAPHS

(71) Applicant: Accenture Global Solutions Limited, Dublin (IE)

(72) Inventors: Sumit Pai, Dublin (IE); Luca Costabello, Newbridge (IE)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 852 days.

(21) Appl. No.: 18/047,446

(22) Filed: Oct. 18, 2022

(65) Prior Publication Data

US 2024/0127909 A1 Apr. 18, 2024

(51) Int. Cl.
*G06N 5/022* (2023.01)
*G16C 20/50* (2019.01)

(52) U.S. Cl.
CPC ............. *G16C 20/50* (2019.02); *G06N 5/022* (2013.01)

(58) Field of Classification Search
CPC .................................................... G06N 20/00
See application file for complete search history.

(56) References Cited

U.S. PATENT DOCUMENTS

| | | | |
|---|---|---|---|
| 12,072,918 B1* | 8/2024 | Newman ................ | G06N 3/045 |
| 2004/0023300 A1* | 2/2004 | Grabe ................... | G16B 30/00 435/7.1 |
| 2019/0303535 A1* | 10/2019 | Fokoue-Nkoutche ...................... G16B 40/00 |
| 2020/0057946 A1* | 2/2020 | Singaraju ............... G06N 5/041 |
| 2023/0386500 A1* | 11/2023 | Sun ........................ G06N 3/045 |
| 2024/0121074 A1* | 4/2024 | Adir .................... H04L 63/0428 |
| 2025/0131694 A1* | 4/2025 | Iscen ................... G06V 10/761 |

OTHER PUBLICATIONS

Trouillon et al., "Complex Embeddings for Simple Link Prediction," International Conference on Machine Learning, 2016, 10 Pages.

Bordes et al., "Translating Embeddings for Modeling Multi-relational Data," Advances in Neural Information Processing Systems, 2013, 9 Pages.

(Continued)

*Primary Examiner* — Kamran Afshar
*Assistant Examiner* — Kyle Allman Thompson
(74) *Attorney, Agent, or Firm* — Mannava & Kang, P.C.

(57) ABSTRACT

A device may train a KGE model based on an initial knowledge graph, and may generate an initial embedding matrix based on training the KGE model. The device may receive a new KG representing new information, and may convert the new KG to new KG triples. The device may generate corruption data based on the new KG triples, and may generate embeddings based on the new embedding matrix and the corruption data. The device may process the embeddings, with the KGE model, to generate scores and a loss, and may regularize the embeddings and the scores/loss for seen and unseen concepts. The device may calculate a regularized loss based on regularizing the embeddings, the scores, and the loss, and may calculate an incremental learning loss based on the loss and the regularized loss. The device may train the KGE model based on the scores and the incremental learning loss.

20 Claims, 14 Drawing Sheets

400

405 — Train a knowledge graph embedding (KGE) model based on an initial knowledge graph representing information 410 — Generate an initial embedding matrix based on training the KGE model 415 — Receive a new knowledge graph representing new information 420 — Convert the new knowledge graph to a new embedding matrix with an input layer of the KGE model 425 — Generate corruption triples based on new knowledge graph triples, of the new embedding matrix, and with a corruption generation layer of the KGE model 430 — Generate embeddings based on the new knowledge graph triples and the corruption triples and with an embedding lookup layer of the KGE model 435 — Process the embeddings, with the KGE model, to generate scores and a loss 440 — Regularize the embeddings for seen and unseen concepts 445 — Calculate a regularized loss based on regularizing the embeddings 450 — Calculate an incremental learning loss based on the loss and the regularized loss 455 — Train the KGE model based on the scores and the incremental learning loss to generate a trained KGE model

(56) References Cited

OTHER PUBLICATIONS

Hogan et al., "Knowledge Graphs," Synthesis Lectures on Data, Semantics, and Knowledge, 2021, 135 Pages.

Galkin et al., "Nodepiece: Compositional and Parameterefficient Representations of Large Knowledge Graphs, " Conference Paper at ICLR, 2022, 25 Pages.

Biesialska et al., "Continual Lifelong Learning in Natural Language Processing: A Survey," arXiv preprint, 2020, 19 Pages.

Hamaguchi et al., "Knowledge Transfer for Out-of-Knowledge-Base Entities: A Graph Neural Network Approach," sciarXiv: 1706.05674v2, 2017, 7 Pages.

Janik et al., "Methods and systems for approximating embeddings of out-of-knowledge graph entities for link prediction In knowledge graph," 2021, 42 Pages.

Galkin et al., "NodePiece: Tokenizing Knowledge Graphs," Towards Data Science, 2021, 14 Pages.

Zhu et al., "Neural Bellman-Ford Networks: A General Graph Neural Network Framework for Link Prediction," 35th Conference on Neural Information Processing Systems, 2021, 15 Pages.

Schlichtkrull et al., "Modeling Relational Data with Graph Convolutional Networks," arXiv:1703.06103v4, 2017, 9 Pages.

* cited by examiner

100

Initial Knowledge Graph

Data structure

105
Receive an initial knowledge graph representing information between diseases, genes, gene variants, biological processes, and proteins

110
Convert the initial knowledge graph to an initial embedding matrix with an input layer of a knowledge graph embedding (KGE) model Training system

125

Process the initial embeddings and a loss, with the KGE model, to generate a trained KGE model where the initial embeddings are trained based on the initial knowledge graph

100

New Knowledge Graph

135
Convert the new knowledge graph to a new embedding matrix based on new triples and the initial embedding matrix Training system

130
Receive a new knowledge graph representing new information between diseases, genes, gene variants, biological processes, and proteins Data structure

100

165

Train the KGE model based on the scores and the incremental learning loss to generate a trained KGE model Trained KGE model Train KGE model Incremental learning loss Training system

170
Merge the initial embedding matrix and the new embedding matrix to generate a final embedding matrix for the trained KGE model Final embedding matrix Merge matrices New embedding matrix Initial embedding matrix Training system

100

INCREMENTALLY TRAINING A KNOWLEDGE GRAPH EMBEDDING MODEL FROM BIOMEDICAL KNOWLEDGE GRAPHS

BACKGROUND

Current methods of new drug discovery are time consuming and expensive. Machine learning may be utilized to discover new drugs. Machine learning is a type of artificial intelligence that allows software applications to become more accurate at predicting outcomes without being explicitly programmed.

SUMMARY

Some implementations described herein relate to a method. The method may include training a knowledge graph embedding (KGE) model based on an initial knowledge graph representing information, and generating an initial embedding matrix based on training the KGE model. The method may include receiving a new knowledge graph representing new information, and converting the new knowledge graph to a new embedding matrix with an input layer of the KGE model. The method may include generating corruption triples based on new knowledge graph triples, of the new embedding matrix, and with a corruption generation layer of the KGE model, and generating embeddings based on the new knowledge graph triples and the corruption triples and with an embedding lookup layer of the KGE model. The method may include processing the embeddings, with the KGE model, to generate scores and a loss, and regularizing the embeddings for seen and unseen concepts. The method may include calculating a regularized loss based on regularizing the embeddings, and calculating an incremental learning loss based on the loss and the regularized loss. The method may include training the KGE model based on the scores and the incremental learning loss to generate a trained KGE model.

Some implementations described herein relate to a device. The device may include one or more memories and one or more processors coupled to the one or more memories. The one or more processors may be configured to train a KGE model based on an initial knowledge graph representing information, and generate an initial embedding matrix based on training the KGE model. The one or more processors may be configured to receive a new knowledge graph representing new information, and convert the new knowledge graph to a new embedding matrix with an input layer of the KGE model. The one or more processors may be configured to generate corruption triples based on new knowledge graph triples, of the new embedding matrix, and with a corruption generation layer of the KGE model, and generate embeddings based on the new knowledge graph triples and the corruption triples and with an embedding lookup layer of the KGE model. The one or more processors may be configured to process the embeddings, with the KGE model, to generate scores and a loss, and regularize the embeddings for seen and unseen concepts. The one or more processors may be configured to calculate a regularized loss based on regularizing the embeddings, and calculate an incremental learning loss based on the loss and the regularized loss. The one or more processors may be configured to train the KGE model based on the scores and the incremental learning loss to generate a trained KGE model.

Some implementations described herein relate to a non-transitory computer-readable medium that stores a set of instructions for a device. The set of instructions, when executed by one or more processors of the device, may cause the device to train a KGE model based on an initial knowledge graph representing information, and generate an initial embedding matrix based on training the KGE model. The set of instructions, when executed by one or more processors of the device, may cause the device to receive a new knowledge graph representing new information, and convert the new knowledge graph to a new embedding matrix with an input layer of the KGE model. The set of instructions, when executed by one or more processors of the device, may cause the device to generate corruption triples based on new knowledge graph triples, of the new embedding matrix, and with a corruption generation layer of the KGE model, and generate embeddings based on the new knowledge graph triples and the corruption triples and with an embedding lookup layer of the KGE model. The set of instructions, when executed by one or more processors of the device, may cause the device to process the embeddings, with the KGE model, to generate scores and a loss, and regularize the embeddings for seen and unseen concepts. The set of instructions, when executed by one or more processors of the device, may cause the device to calculate a regularized loss based on regularizing the embeddings, and calculate an incremental learning loss based on the loss and the regularized loss. The set of instructions, when executed by one or more processors of the device, may cause the device to train the KGE model based on the scores and the incremental learning loss to generate a trained KGE model.

DETAILED DESCRIPTION

Figure 1A:
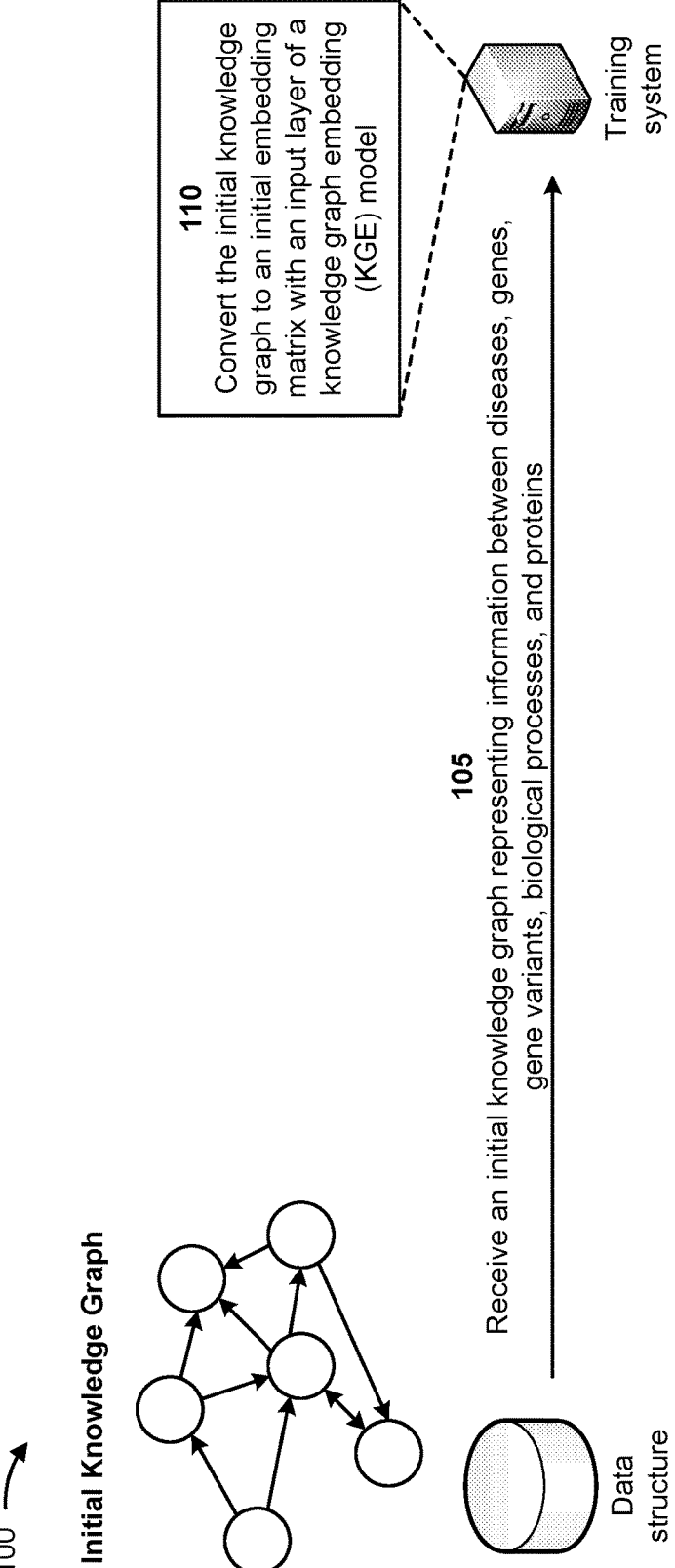
FIGS. 1A-1K are diagrams of an example implementation described herein.

The following detailed description of example implementations refers to the accompanying drawings. The same reference numbers in different drawings may identify the same or similar elements.

In-silico hypothesis generation is the adoption of machine learning models to create plausible biological hypotheses from large biomedical datasets. Such hypotheses are inferred from the data stored in the datasets and are provided to researchers to validate the hypotheses with laboratory studies. A knowledge graph is a graph dataset of directed, label edges that connect nodes representing concepts (e.g., people, products, companies, genes, proteins, and/or the like). A knowledge graph may be utilized to represent biomedical datasets. A triple is a fact or a link defined as $t=(s, p, o)$, where s is a subject, p is a predicate, and o is an object. An embedding is a k-dimensional vector of real numbers that represents either a node or an edge type of a knowledge graph. Embeddings are learned by neural networks (e.g., a KGE model) and serve as internal representations of concepts learned from the knowledge graph. A KGE model is a neural network architecture (e.g., a neural link predictor) that learns vector representations (e.g., embeddings) of concepts from a training a knowledge graph to predict missing, unseen links between nodes. The training phase of a KGE model attempts to minimize a loss layer that includes a scoring layer (e.g., a method-specific function that assigns a plausibility score to a triple). The goal of the training phase is to learn optimal embeddings, such that the scoring layer is able to assign high scores to positive statements and low scores to statements unlikely to be true.

Current techniques require a full retraining of the KGE model when new edges added between existing nodes of a knowledge graph are learned, after initially training the KGE model. This is a severe limitation when operating with a large knowledge graph that grows in size, such as a knowledge graph based on a biomedical knowledge dataset. For example, a KGE model may be trained based on a large biomedical knowledge graph. Such training requires considerable time and resources. A new triple (e.g., an edge) may be added to the knowledge graph, and the new triple may be associated with nodes already existing in the knowledge graph. However, to incorporate the new triple between two existing nodes of the knowledge graph, requires a full retraining of the KGE model. Current techniques also require a full retraining of the KGE model when new triples, associated with nodes and relations, do not occur in an original knowledge graph since embeddings of the new triples have not been learned by the KGE model. For example, a KGE model may be trained based on a large biomedical knowledge graph. A new triple may be added to the knowledge graph, and the new triple may not be associated with any information in the knowledge graph. The KGE model failed to learn an embedding for the new triple during training. Therefore, to incorporate the new triple in the knowledge graph, requires a full retraining of the KGE model.

Therefore, current techniques for updating a KGE model consume computing resources (e.g., processing resources, memory resources, communication resources, and/or the like), networking resources, and/or the like associated with fully retraining the KGE model when new information associated with existing information of a knowledge graph is added to the knowledge graph, fully retraining the KGE model when new information not associated with existing information of the knowledge graph is added to the knowledge graph, handling large datasets represented by knowledge graphs, updating large knowledge graphs, and/or the like.

Some implementations described herein relate to a training system that incrementally trains a KGE model from biomedical knowledge graphs. For example, the training system may train a KGE model based on an initial knowledge graph representing information, and may generate an initial embedding matrix based on training the KGE model. The training system may receive a new knowledge graph representing new information, and may convert the new knowledge graph to a new embedding matrix with an input layer of the KGE model. The training system may generate corruption data based on the new embedding matrix and with a corruption generation layer of the KGE model, and may generate embeddings based on the new embedding matrix and the corruption data and with an embedding lookup layer of the KGE model. The training system may process the embeddings and a loss, with the KGE model, to generate scores, and may regularize the embeddings and the loss for seen and unseen concepts. The training system may calculate a regularized loss based on regularizing the embeddings and the loss, and may calculate an incremental learning loss based on the loss and the regularized loss. The training system may train the KGE model based on the scores and the incremental learning loss to generate a trained KGE model, and may merge the initial embedding matrix and the new embedding matrix to generate a final embedding matrix for the trained KGE model.

In this way, the training system incrementally trains a KGE model from biomedical knowledge graphs. For example, the training system may provide a KGE model that generates new in-silico hypotheses by incrementally learning from an input knowledge graph that grows in size. Once the KGE model has been trained, the training system may receive new information associated with the knowledge graph, and may determine embeddings for the new information. The training system may also update existing embeddings of the knowledge graph based on the new information. The training system may incrementally learn embeddings of unseen (e.g., unknown) entities and/or relations, and may update embeddings of seen (e.g., known) entities and/or relations with new information. Thus, the training system addresses the technical problems associated with the current techniques for updating a KGE model. This, in turn, conserves computing resources, networking resources, and/or the like that would otherwise have been consumed in fully retraining the KGE model when new information associated with existing information of a knowledge graph is added to the knowledge graph, fully retraining the KGE model when new information not associated with existing information of the knowledge graph is added to the knowledge graph, handling large datasets represented by knowledge graphs, updating large knowledge graphs, and/or the like.

FIGS. 1A-1K are diagrams of an example 100 associated with incrementally training a KGE model from biomedical knowledge graphs. As shown in FIGS. 1A-1K, example 100 includes a training system associated with a data structure. The training system may include a system that incrementally trains a KGE model from biomedical knowledge graphs. Further details of the training system and the data structure are provided elsewhere herein.

As shown in FIG. 1A, and by reference number 105, the training system may receive an initial knowledge graph representing information. For example, a data structure (e.g., a database, a table, a list, and/or the like) may store the initial knowledge graph. In some implementations, the training system may continuously receive the initial knowledge graph from the data structure, may periodically receive the initial knowledge graph from the data structure, may receive the initial knowledge graph from the data structure based on providing a request to the data structure, and/or the like.

The initial knowledge graph may include a graph dataset of directed, label edges that connect nodes representing concepts (e.g., people, products, companies, genes, proteins, and/or the like). The initial knowledge graph may be utilized to represent biomedical datasets that include information between diseases, genes, gene variants, biological processes, proteins, and/or the like. In some implementations, the initial knowledge graph may represent a database of information about compounds (e.g., to be utilized for drug discovery). The initial knowledge graph may enable more properties and relationships around compounds to be represented, even properties and/or relationships that may not seem directly related to the compounds. Furthermore, the training system may utilize embeddings (e.g., which include all properties of compounds) when training a latent space instead of having to select a subset of properties due to data limitations. In some implementations, the initial knowledge graph may represent data associated with human resources (e.g., for career progression, role transition, hiring, and/or the like), a retail sector for product recommendation, a manufacturing sector for product reformulation, and/or the like.

As further shown in FIG. 1A, and by reference number 110, the training system may convert the initial knowledge graph to an initial embedding matrix with an input layer of a KGE model. For example, the training system may provide the initial knowledge graph to the input layer of the KGE model, and the input layer may convert the initial knowledge graph to the initial embedding matrix that includes initial triples. Each initial triple (t) may be represented as t=(s, p, o), where s is a subject, p is a predicate, and o is an object.

Figure 1B:
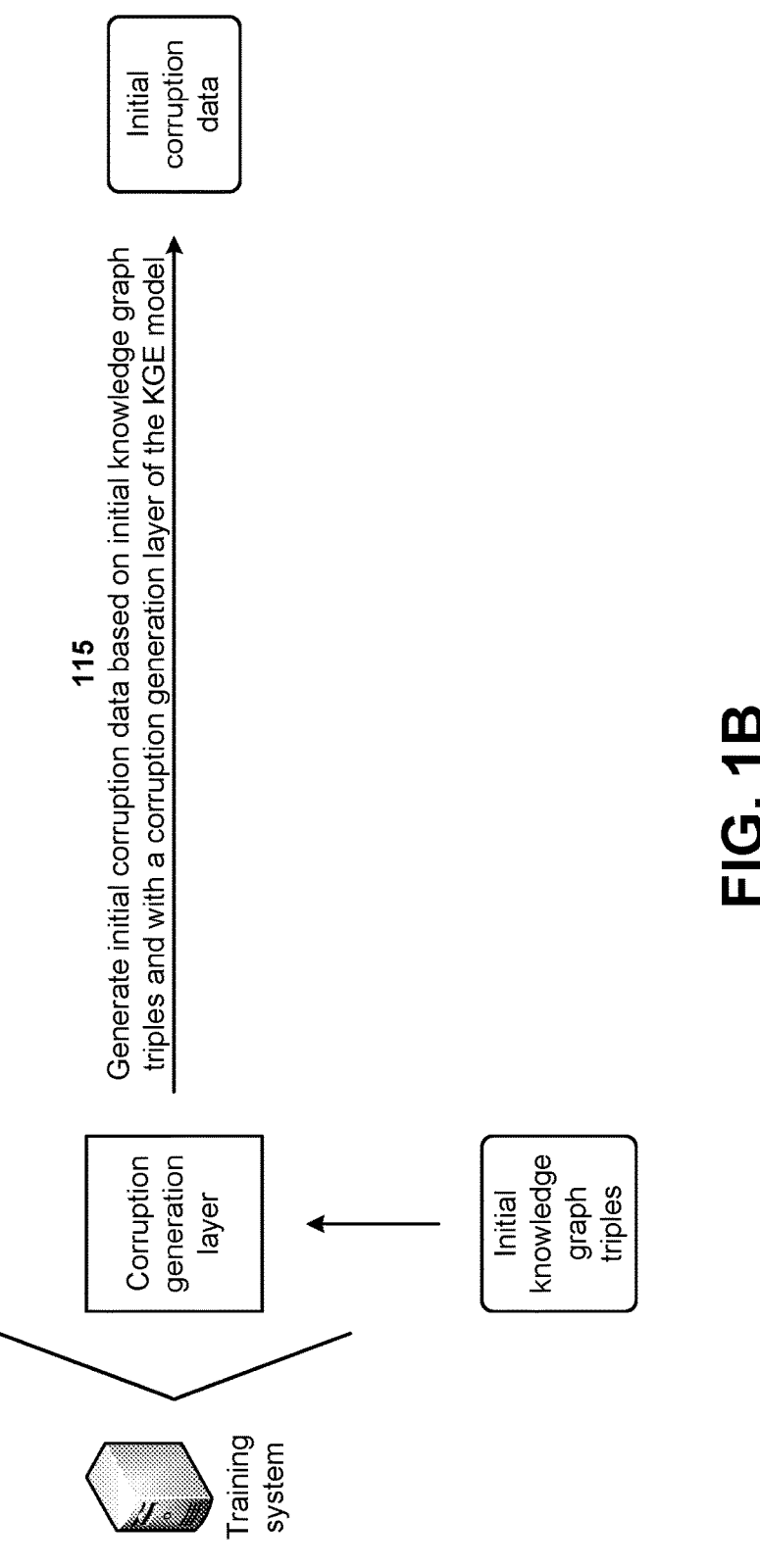

As shown in FIG. 1B, and by reference number 115, the training system may generate initial corruption data based on initial knowledge graph triples of the initial embedding matrix and with a corruption generation layer of the KGE model. For example, the training system may provide the initial embedding matrix to the corruption generation layer of the KGE model, and the corruption generation layer may generate initial corrupt triples (e.g., the initial corruption data) based on the initial embedding matrix. In some implementations, when generating the initial corruption data based on the initial embedding matrix, the corruption generation layer of the KGE model may generate the initial corruption data by randomly replacing subjects or objects of the initial triples with random entities from the initial knowledge graph.

Figure 1C:
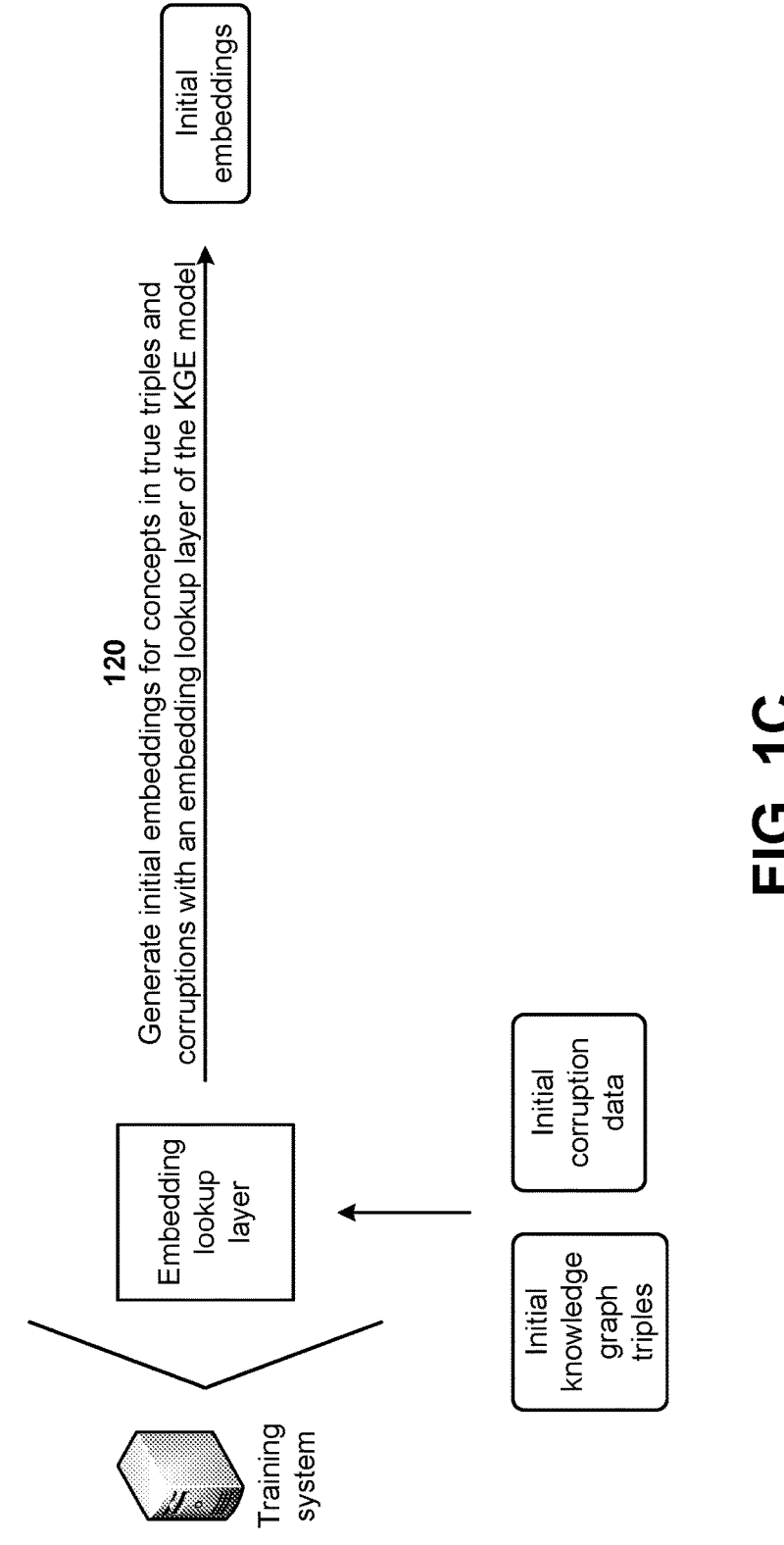

As shown in FIG. 1C, and by reference number 120, the training system may generate initial embeddings for concepts in true triples and corruptions with an embedding lookup layer of the KGE model. For example, the training system may provide the initial embedding matrix and the initial corruption data to the embedding lookup layer of the KGE model, and the embedding lookup layer may generate the initial embeddings based on the initial embedding matrix and the initial corruption data. The initial embeddings may be provided in a d-dimensional space called an embedding space. An initial embedding is a vector of numbers of d dimensions, and each initial triple and/or initial corrupt triple of the initial knowledge graph may be associated with a unique initial embedding. In some implementations, the embedding lookup layer of the KGE model may look up initial embeddings associated with the initial triples and the initial corruption data.

Figure 1D:
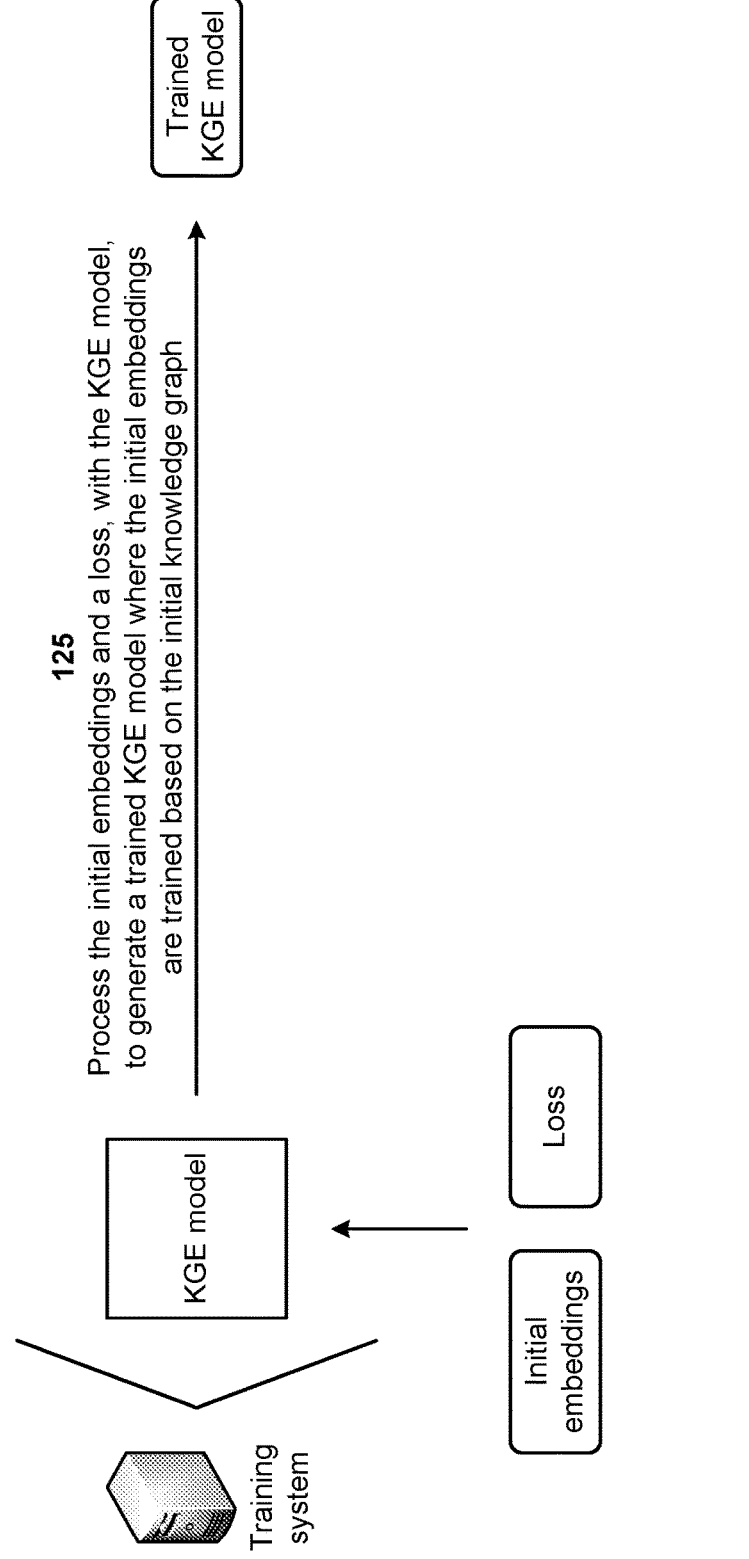

As shown in FIG. 1D, and by reference number 125, the training system may process the initial embeddings and loss, with the KGE model, to generate a trained KGE model where the initial embeddings are trained based on the initial knowledge graph. For example, the training system may provide the initial embeddings associated with the initial triples and the loss to the scoring layer of the KGE model, and the scoring layer may generate the trained KGE model based on the initial embeddings associated with the initial triples and the loss. In some implementations, the training system may process the initial embeddings and the loss, with a scoring function, to calculate initial scores. The scoring function may include a TransE scoring function (e.g., a translation-based embedding model), a DistMult scoring function (e.g., a neural tensor network with a diagonal matrix operator), a ComplEx technique (e.g., a complex embeddings scoring function), a HolE scoring function (e.g., holographic embeddings scoring function), a RotatE scoring function, a ConvE scoring function, a ConvKB scoring function, and/or the like. In some implementations, the greater a score, the greater the chances that an initial triple is factually correct. The scoring layer of the KGE model may provide a way to assign a plausibility score to each fact of the initial knowledge graph.

The training system may provide initial scores to the loss layer of the KGE model, and the loss layer may determine the loss based on the initial scores. In some implementations, the loss layer may utilize initial scores associated with positive initial triples and corresponding initial corruption data when determine the loss.

Figure 1E:
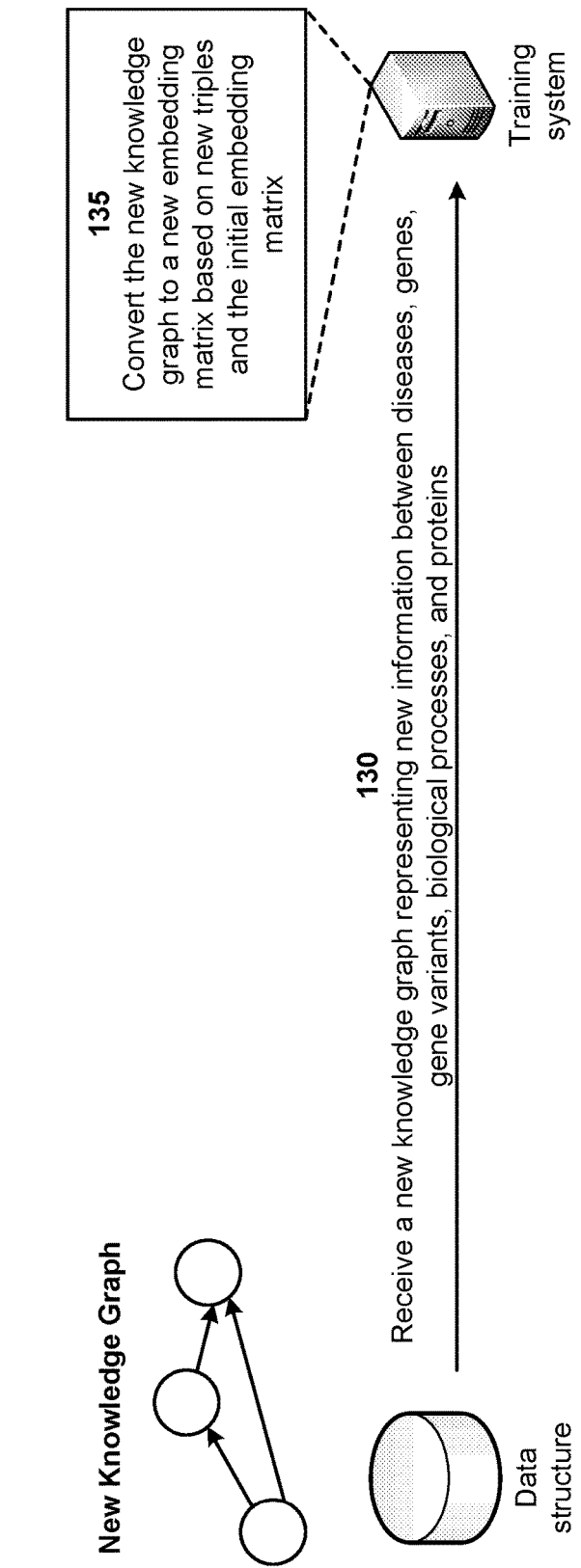

As shown in FIG. 1E, and by reference number 130, the training system may receive a new knowledge graph representing new information. For example, the data structure may store the new knowledge graph. In some implementations, the training system may continuously receive the new knowledge graph from the data structure, may periodically receive the new knowledge graph from the data structure, may receive the new knowledge graph from the data structure based on providing a request to the data structure, and/or the like.

The new knowledge graph may include a graph dataset of directed, label edges that connect nodes representing concepts (e.g., people, products, companies, genes, proteins, and/or the like). The new knowledge graph may be utilized to represent biomedical datasets that include information between diseases, genes, gene variants, biological processes, proteins, and/or the like. In some implementations, the new knowledge graph may represent a database of information about compounds (e.g., to be utilized for drug discovery). The new knowledge graph may include seen (e.g., known) information included in the initial knowledge graph and unseen (e.g., unknown) information not included in the initial knowledge graph, may include only unseen information, and/or the like.

As further shown in FIG. 1E, and by reference number 135, the training system may convert the new knowledge graph to a new embedding matrix based on new triples and the initial embedding matrix. For example, the training system may provide the new knowledge graph to the input layer of the KGE model, and the input layer may convert the new knowledge graph to the new embedding matrix with new triples. Each new triple (t) may be represented as t=(s, p, o), where s is a subject, p is a predicate, and o is an object.

Figure 1F:
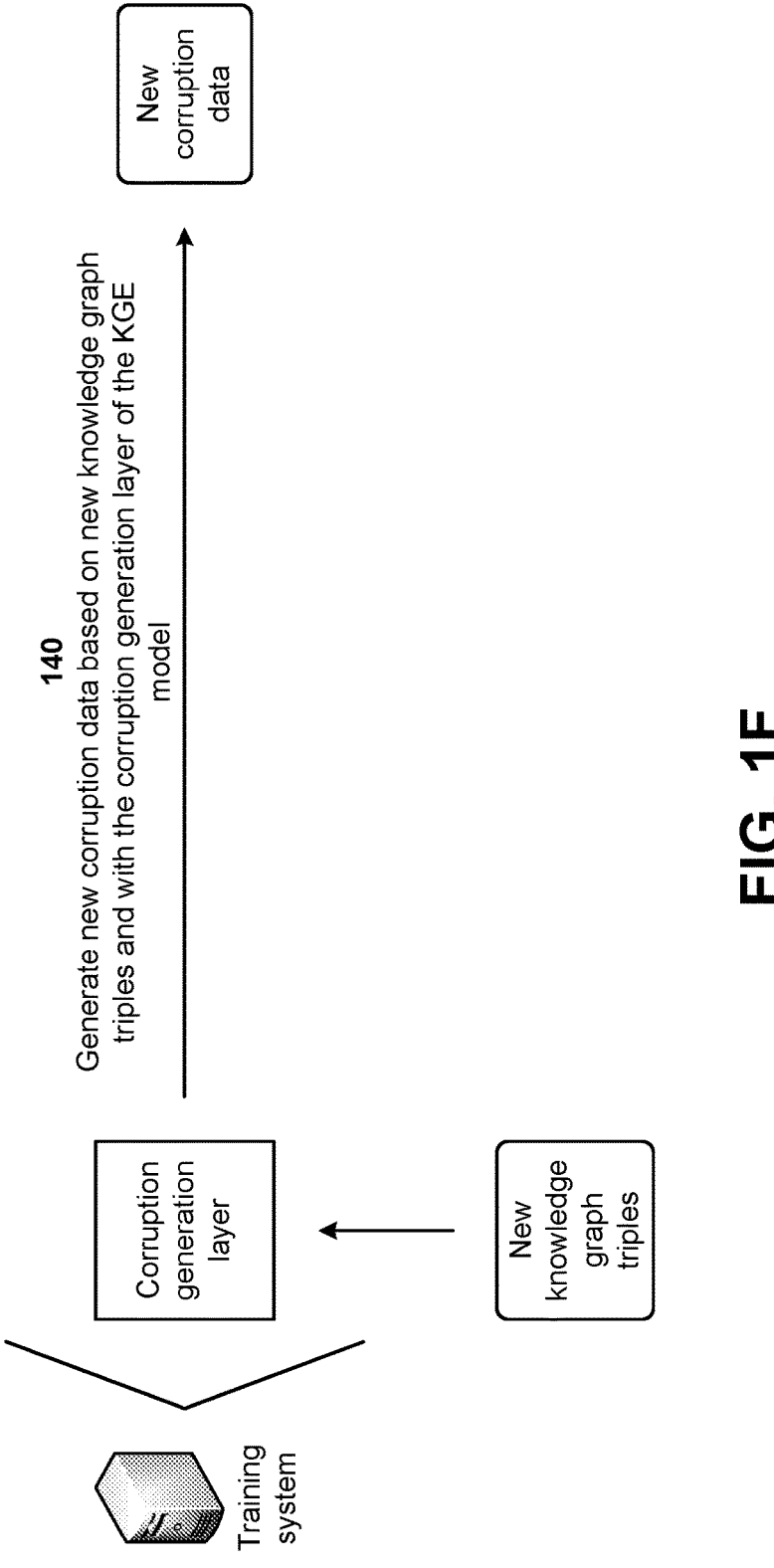

As shown in FIG. 1F, and by reference number 140, the training system may generate new corruption data based on new knowledge graph triples, of the new embedding matrix, and with the corruption generation layer of the KGE model. For example, the training system may provide the new embedding matrix to the corruption generation layer of the KGE model, and the corruption generation layer may generate new corrupt triples (e.g., the new corruption data) based on the new embedding matrix. In some implementations, when generating the new corruption data based on the new embedding matrix, the corruption generation layer of the KGE model may generate the new corruption data by randomly replacing subjects or objects of the new embedding matrix with random entities from the new knowledge graph.

Figure 1G:
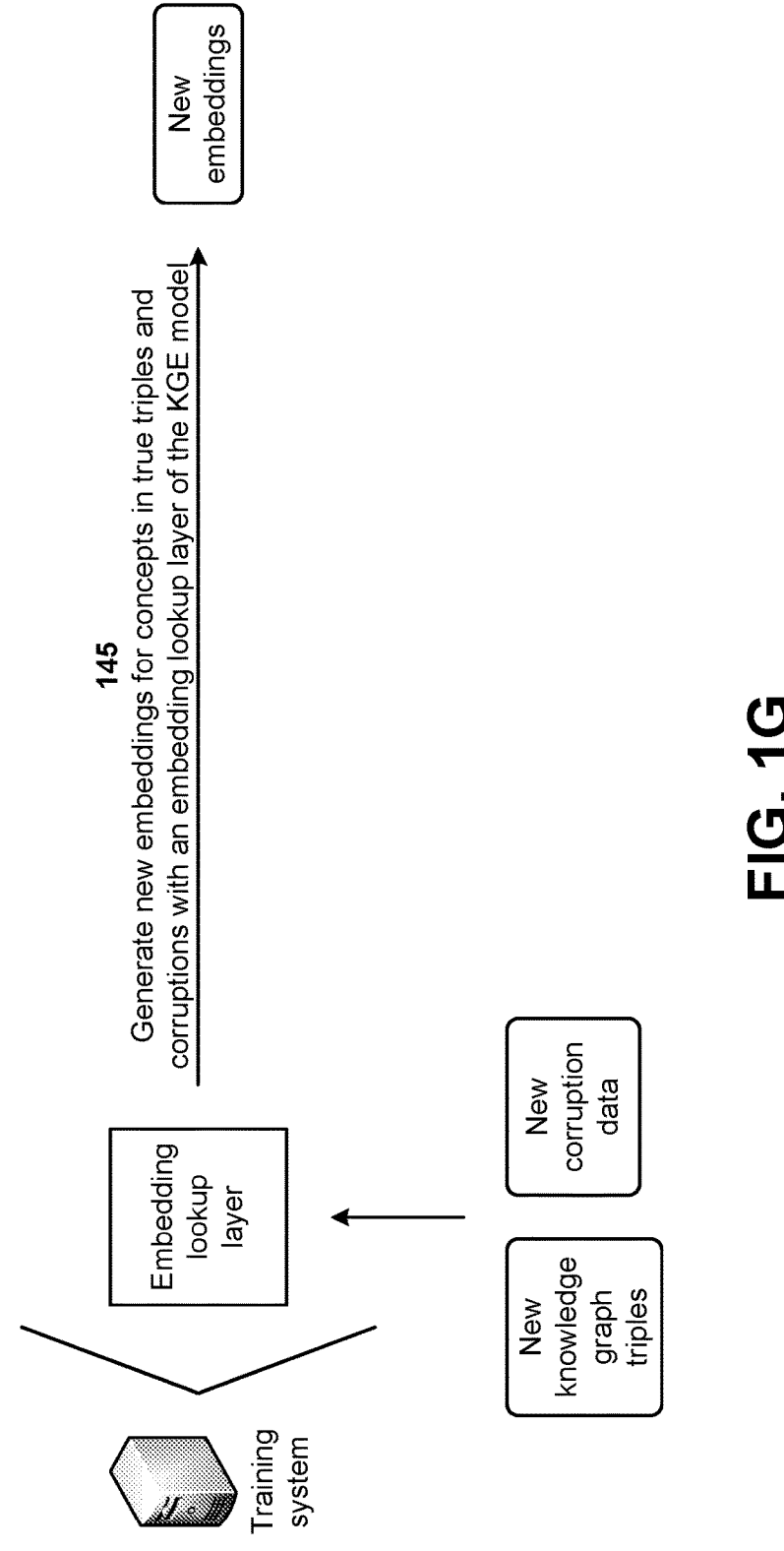

As shown in FIG. 1G, and by reference number 145, the training system may generate new embeddings for concepts in true triples and corruptions with an embedding lookup layer of the KGE model. For example, the training system may provide the new embedding matrix and the new corruption data to the embedding lookup layer of the KGE model, and the embedding lookup layer may generate the new embeddings based on the new embedding matrix and the new corruption data. The new embeddings may be provided in a d-dimensional space. A new embedding is a vector of numbers of d dimensions, and each new triple and/or new corrupt triple of the new knowledge graph may be associated with a new unique embedding.

In some implementations, when generating the new embeddings based on the new embeddings and the new corruption data, the training system may identify initial entities in the initial knowledge graph most similar to new entities in the new knowledge graph, and may retrieve initial embeddings associated with the initial entities. The training system may add random noise to the initial embeddings to generate the new embeddings. In some implementations, when identifying the initial entities in the initial knowledge graph most similar to the new entities in the new knowledge graph, the training system may identify the initial entities most similar to the new entities based on an intersection over union (IOU) determined for each of the initial entities and each of the new entities.

For example, for each new entity $$\left(c_{unseen}^{i}\right)$$

in the new knowledge graph, the training system may identify an initial entity $$\left(c_{seen}^{j}\right)$$

in the initial knowledge graph which has a greatest IOU with the new entity. IOU is a method to find a similar entity ($N_1$) to a new entity ($N_2$) and may be determined as follows:

$$IOU(N_1, N_2) = \frac{\#Intersection(Incoming\ Relations(N_1, N_2)) + \#Intersection(Outgoing\ Relations(N_1, N_2))}{\#Union(Incoming\ Relations(N_1, N_2)) + \#Union(Outgoing\ Relations(N_1, N_2))}.$$

The training system may retrieve an initial embedding $$\left(e_{seen}^{j}\right)$$

associated with the initial entity. The training system may add Gaussian random noise to the initial embedding $$\left(e_{unseen}^{i} = e_{seen}^{j} + N\!\left(0, \sum\right)\right)$$

and may utilize the result as a new embedding. The training system may generate new embeddings in a similar manner, and may create the new embedding matrix ($E_{unseen}$) based on the new embeddings. For new relations, the training system may randomly initialize embeddings of the new relations $$\left(r_{unseen}^{j} = N\!\left(0, \sum\right)\right).$$

Figure 1H:
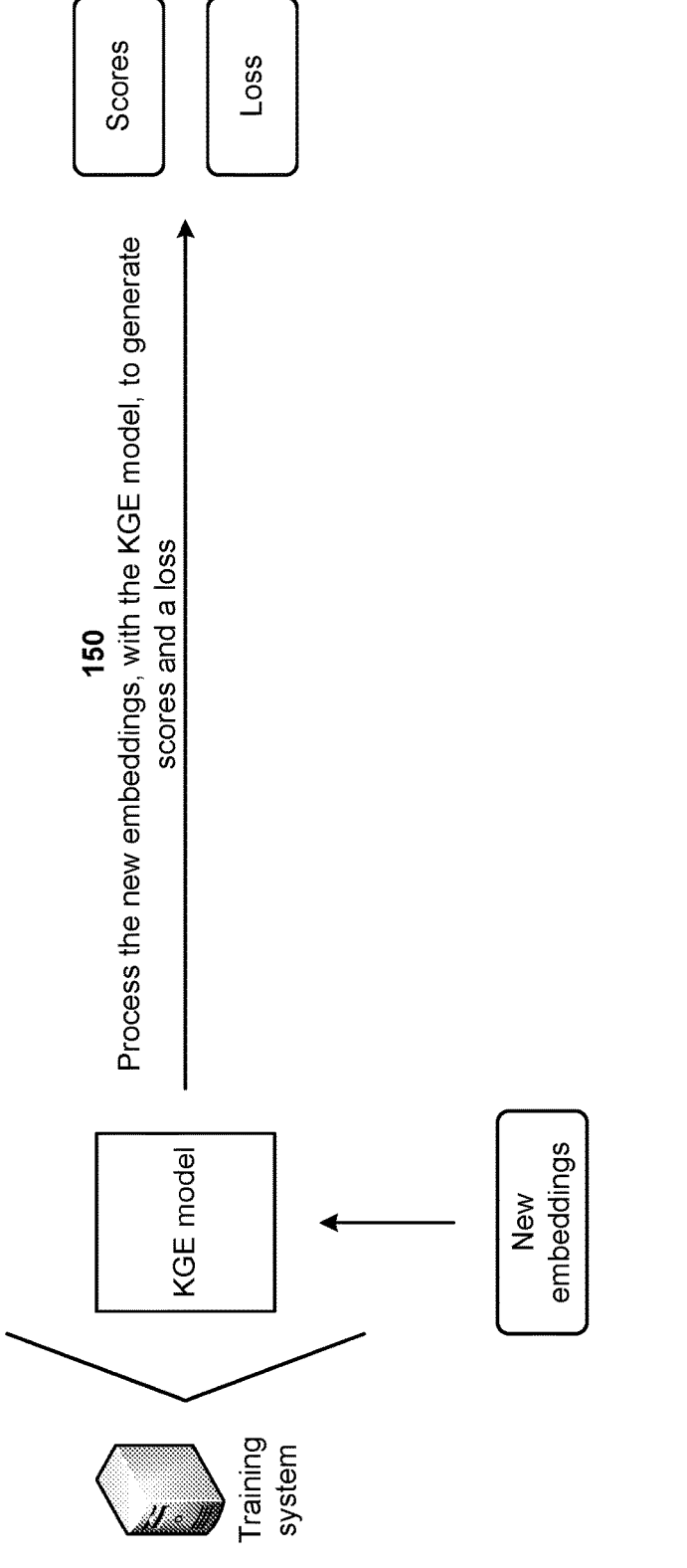

As shown in FIG. 1H, and by reference number 150, the training system may process the new embeddings, with the KGE model, to generate scores and a loss. For example, the training system may provide the new embeddings associated with the new triples and the loss to the scoring layer of the KGE model, and the scoring layer may calculate the scores (e.g., inference outputs) based on the new embeddings associated with the new triples and the loss. In some implementations, when calculating the scores based on the new embeddings, the training system may process the new embeddings, with a scoring function, to calculate the scores. The scoring function may include the TransE scoring function, a DistMult scoring function, a ComplEx technique, a HolE scoring function, and/or the like. In some implementations, the greater a score, the greater the chances that a new triple is factually correct. The scoring layer of the KGE model may provide a way to assign a plausibility score to each fact of the new knowledge graph.

The training system may provide the scores to the loss layer of the KGE model, and the loss layer may determine the loss based on the scores. In some implementations, the loss layer may utilize scores associated with positive new triples and corresponding new corruption data when determine the loss. In some implementations, the loss may correspond to a triple loss ($L_{KGE}$).

Figure 1I:
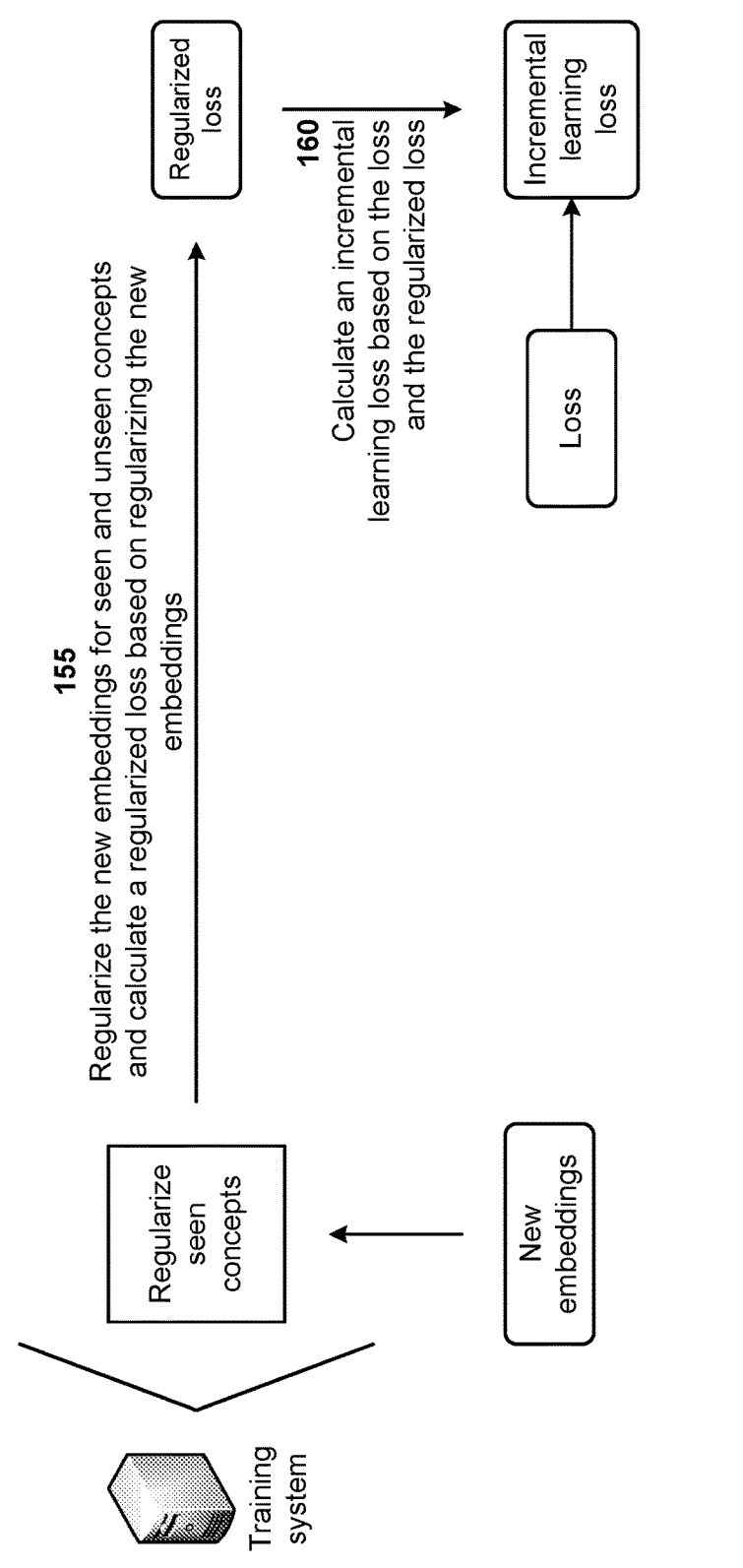

As shown in FIG. 1I, and by reference number 155, the training system may regularize the new embeddings for seen and unseen concepts and may calculate a regularized loss based on regularizing the new embeddings. For example, depending on which entity (e.g., subject, object, or both) in a new triple is seen (e.g., present in the initial knowledge graph), the training system may penalize a new embedding associated with the new triple with a high weight ($w_{high}$). For the unseen entities, the training system may penalize a new embedding with a low weight ($w_{low}$). The training system may calculate the regularized loss as follows:

$$L_{regularized} = w_{high} * MSE\!\left(e_{seen}^{\langle i,start\rangle}, e_{seen}^{\langle i,current\rangle}\right) + w_{low} * MSE\!\left(e_{unseen}^{\langle j,start\rangle}, e_{unseen}^{\langle j,current\rangle}\right),$$

where MSE is a mean square error. In some implementations, the training system may utilize a similar regularization for relations:

$$L_{regularized}^{reln} = w_{high} * MSE\!\left(r_{seen}^{\langle i,start\rangle}, r_{seen}^{\langle i,current\rangle}\right) + w_{low} * MSE\!\left(r_{unseen}^{\langle j,start\rangle}, r_{unseen}^{\langle j,current\rangle}\right).$$

In some implementations, when regularizing the new embeddings for seen and unseen concepts, the training system may apply a first weight ($w_{high}$) to the seen concepts, and may apply a second weight ($w_{low}$) to the unseen concepts. The training system may regularize the new embeddings based on applying the first weight to the seen concepts and applying the second weight to the unseen concepts.

As further shown in FIG. 1I, and by reference number 160, the training system may calculate an incremental learning loss based on the loss and the regularized loss. For example, the training system may add the loss ($L_{KGE}$) and the regularized loss ($L_{regularized}$) together to calculate the incremental learning loss ($L_{inc}$): $L_{inc} = L_{KGE} + L_{regularized}$. With the regularization, the training system may enforce a strong prior over seen entity embeddings such that such embeddings do not significantly change. Thus, new entities may change faster than the older seen entities. With such an approach, for every additional dataset, the training system (e.g., and the KGE model) may incrementally learn such that an initial embedding space may not significantly change.

Figure 1J:
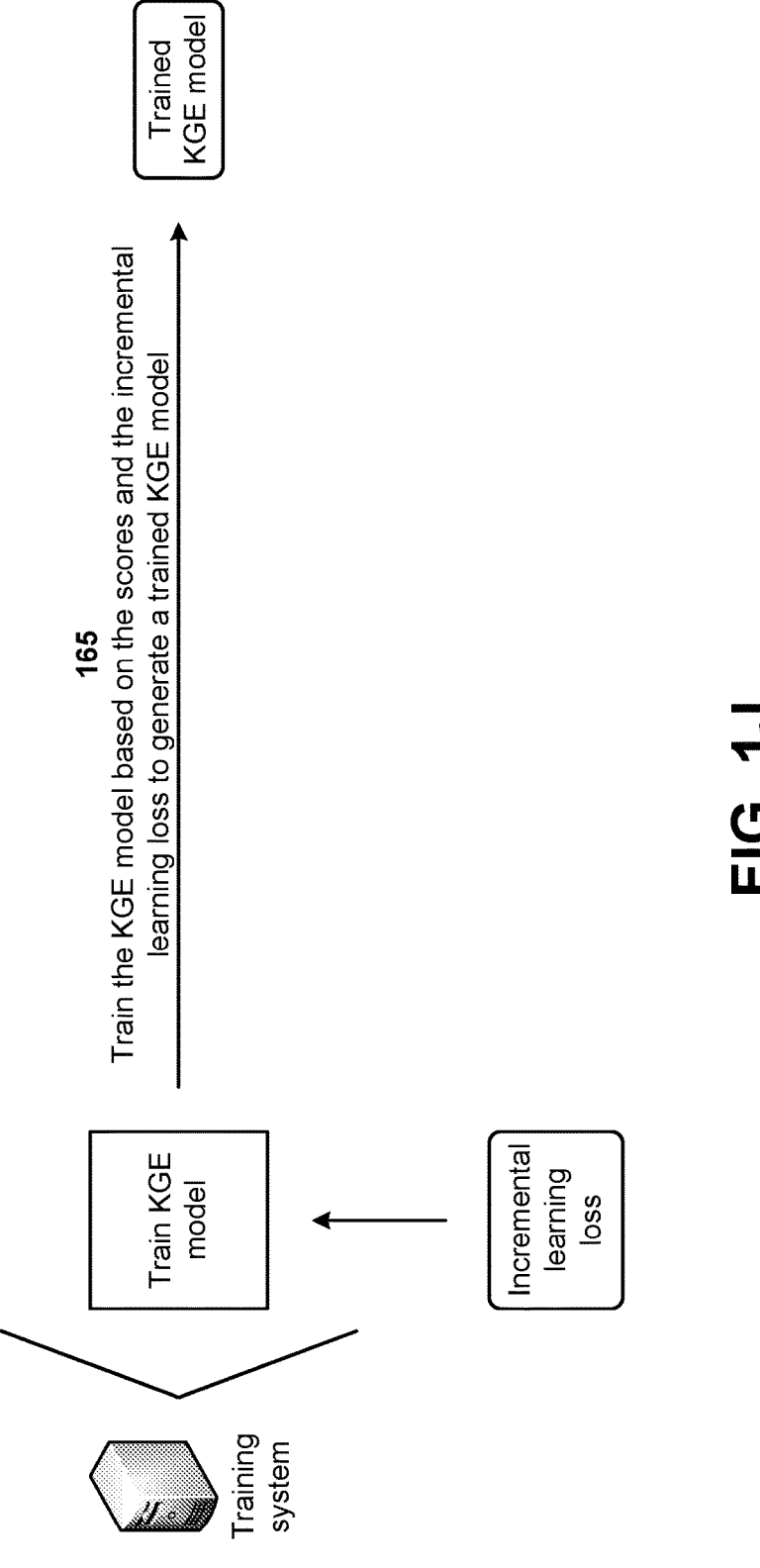

As shown in FIG. 1J, and by reference number 165, the training system may train the KGE model based on the scores and the incremental learning loss to generate a trained KGE model. For example, when training the KGE model based on the scores and the incremental learning loss to generate the trained KGE model, the training system may minimize the incremental learning loss based on the scores, and may generate the trained KGE model based on minimizing the incremental learning loss. The training phase of the KGE model may include minimizing the loss layer (e.g., the incremental learning loss) based on the scoring layer (e.g., the scores). A goals of the training phase is learning optimal embeddings, such that a scoring function is able to assign high scores to positive statements and low scores to statements unlikely to be true. As example, a scoring layer of a TransE scoring function computes a similarity between an embedding of a subject $e_s$, translated by an embedding of a predicate $e_p$, and an embedding of an object $e_o$, using an L2 norm (e.g., Euclidean distance): $f_{TransE}=-\|e_s+e_p-e_o\|_2$. Such a scoring layer may be utilized on positive and negative triples $(t^+, t^-)$ in the loss layer L, that can be, for example, a pairwise margin-based loss, as shown in the equation below:

$$L(\theta) = \sum_{t^+\in G}\sum_{t^-\in N} \max(0, [\gamma + f_m(t^-; \theta) - f_m(t^+; \theta)]),$$

where $\theta$ are the embeddings learned by the KGE model (e.g., the initial embedding matrix), $f_m$ is a model-specific scoring function, $\gamma$ is a margin, and N is a set of negative triples generated with a corruption heuristic.

Figure 1K:
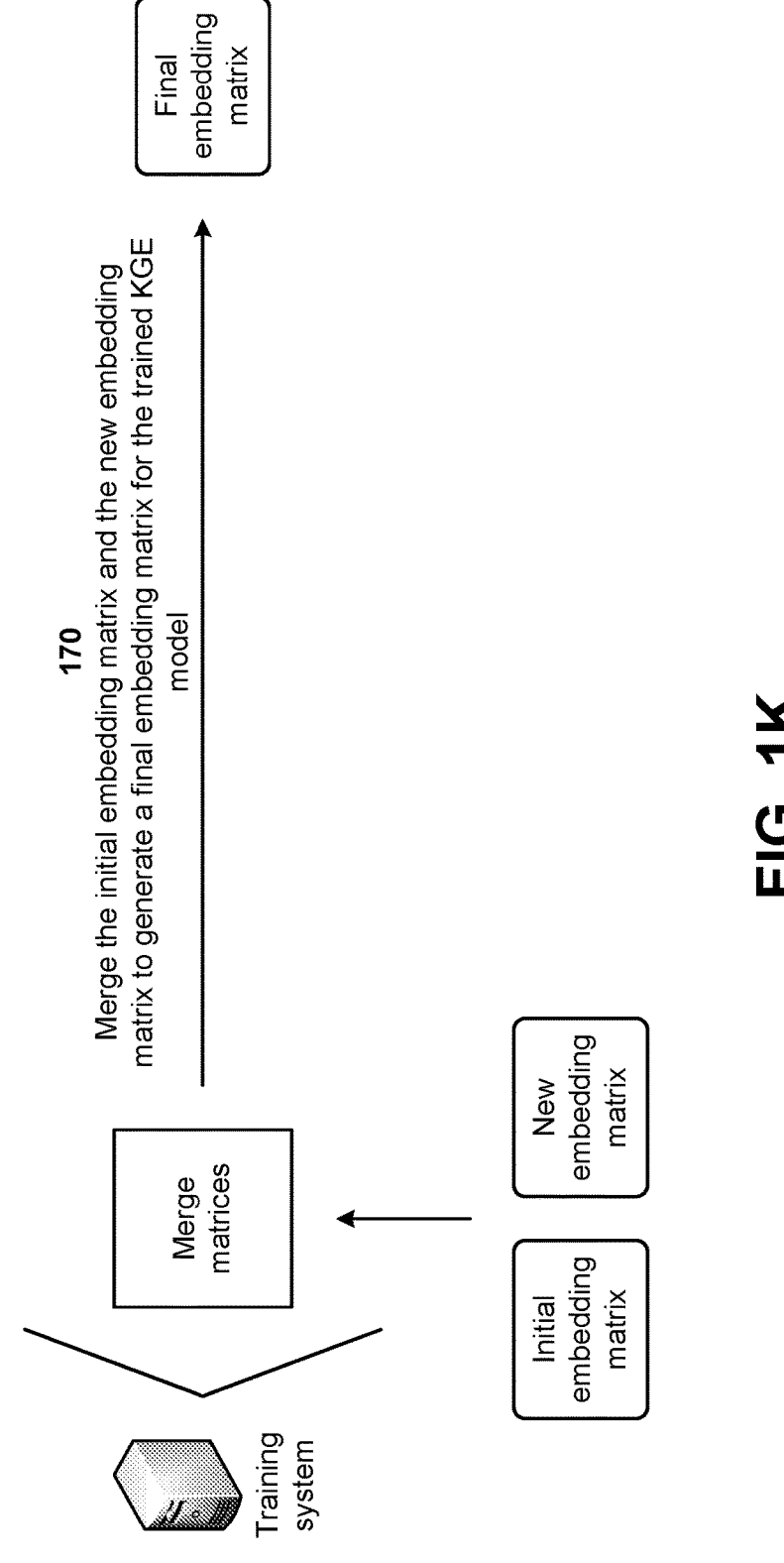

As shown in FIG. 1K, and by reference number 170, the training system may merge the initial embedding matrix and the new embedding matrix to generate a final embedding matrix for the trained KGE model. For example, the training system may merge the initial embedding matrix ($E_{seen}$) and the new embedding matrix ($E_{unseen}$) by concatenating the two matrices together to generate the final embedding matrix $$(E_{seen}^{new}): E_{seen}^{new} = concat(E_{seen}, E_{unseen}).$$

In this way, the training system incrementally trains a KGE model from biomedical knowledge graphs. For example, the training system may provide a KGE model that generates new in-silico hypotheses by incrementally learning from an input knowledge graph that grows in size. Once the KGE model has been trained, the training system may receive new information associated with the knowledge graph, and may determine embeddings for the new information. The training system may also update existing embeddings of the knowledge graph based on the new information. The training system may incrementally learn embeddings of unseen (e.g., unknown) entities and/or relations, and may update embeddings of seen (e.g., known) entities and/or relations with new information. Thus, the training system addresses the technical problems associated with the current techniques for updating a KGE model. This, in turn, conserves computing resources, networking resources, and/or the like that would otherwise have been consumed in fully retraining the KGE model when new information associated with existing information of a knowledge graph is added to the knowledge graph, fully retraining the KGE model when new information not associated with existing information of the knowledge graph is added to the knowledge graph, handling large datasets represented by knowledge graphs, updating large knowledge graphs, and/or the like.

As indicated above, FIGS. 1A-1K are provided as an example. Other examples may differ from what is described with regard to FIGS. 1A-1K. The number and arrangement of devices shown in FIGS. 1A-1K are provided as an example. In practice, there may be additional devices, fewer devices, different devices, or differently arranged devices than those shown in FIGS. 1A-1K. Furthermore, two or more devices shown in FIGS. 1A-1K may be implemented within a single device, or a single device shown in FIGS. 1A-1K may be implemented as multiple, distributed devices. Additionally, or alternatively, a set of devices (e.g., one or more devices) shown in FIGS. 1A-1K may perform one or more functions described as being performed by another set of devices shown in FIGS. 1A-1K.

Figure 2:
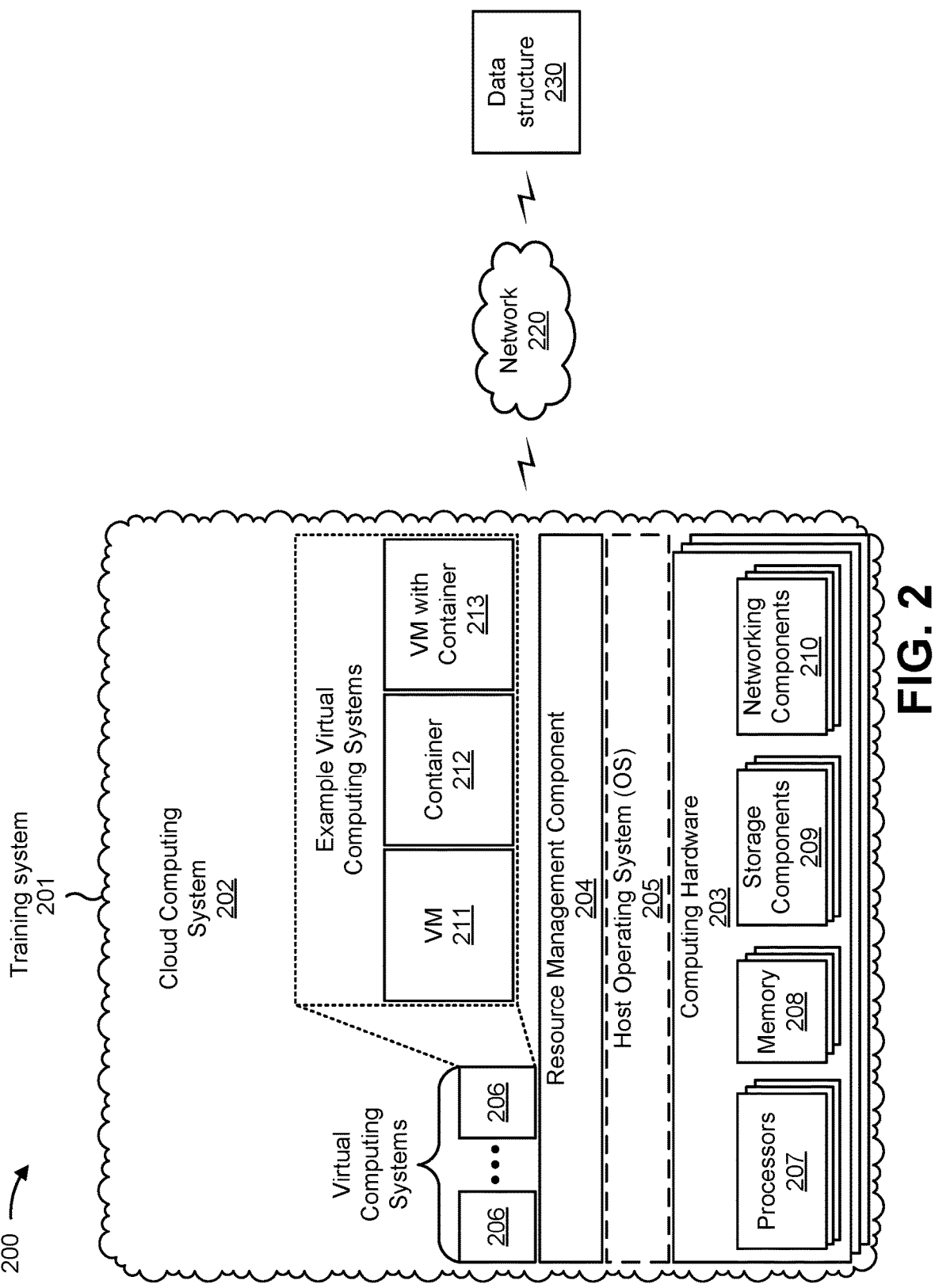
FIG. 2 is a diagram of an example environment in which systems and/or methods described herein may be implemented.

FIG. 2 is a diagram of an example environment 200 in which systems and/or methods described herein may be implemented. As shown in FIG. 2, the environment 200 may include a training system 201, which may include one or more elements of and/or may execute within a cloud computing system 202. The cloud computing system 202 may include one or more elements 203-213, as described in more detail below. As further shown in FIG. 2, the environment 200 may include a network 220 and/or a data structure 230. Devices and/or elements of the environment 200 may interconnect via wired connections and/or wireless connections.

The cloud computing system 202 includes computing hardware 203, a resource management component 204, a host operating system (OS) 205, and/or one or more virtual computing systems 206. The resource management component 204 may perform virtualization (e.g., abstraction) of the computing hardware 203 to create the one or more virtual computing systems 206. Using virtualization, the resource management component 204 enables a single computing device (e.g., a computer, a server, and/or the like) to operate like multiple computing devices, such as by creating multiple isolated virtual computing systems 206 from the computing hardware 203 of the single computing device. In this way, the computing hardware 203 can operate more efficiently, with lower power consumption, higher reliability, higher availability, higher utilization, greater flexibility, and lower cost than using separate computing devices.

The computing hardware 203 includes hardware and corresponding resources from one or more computing devices. For example, the computing hardware 203 may include hardware from a single computing device (e.g., a single server) or from multiple computing devices (e.g., multiple servers), such as multiple computing devices in one or more data centers. As shown, the computing hardware 203 may include one or more processors 207, one or more memories 208, one or more storage components 209, and/or one or more networking components 210. Examples of a processor, a memory, a storage component, and a networking component (e.g., a communication component) are described elsewhere herein.

The resource management component 204 includes a virtualization application (e.g., executing on hardware, such as the computing hardware 203) capable of virtualizing the computing hardware 203 to start, stop, and/or manage the one or more virtual computing systems 206. For example, the resource management component 204 may include a hypervisor (e.g., a bare-metal or Type 1 hypervisor, a hosted or Type 2 hypervisor, and/or the like) or a virtual machine monitor, such as when the virtual computing systems 206 are virtual machines 211. Additionally, or alternatively, the resource management component 204 may include a container manager, such as when the virtual computing systems 206 are containers 212. In some implementations, the resource management component 204 executes within and/or in coordination with a host operating system 205.

A virtual computing system 206 includes a virtual environment that enables cloud-based execution of operations and/or processes described herein using computing hardware 203. As shown, a virtual computing system 206 may include a virtual machine 211, a container 212, a hybrid environment 213 that includes a virtual machine and a container, and/or the like. A virtual computing system 206 may execute one or more applications using a file system that includes binary files, software libraries, and/or other resources required to execute applications on a guest operating system (e.g., within the virtual computing system 206) or the host operating system 205.

Although the training system 201 may include one or more elements 203-213 of the cloud computing system 202, may execute within the cloud computing system 202, and/or may be hosted within the cloud computing system 202, in some implementations, the training system 201 may not be cloud-based (e.g., may be implemented outside of a cloud computing system) or may be partially cloud-based. For example, the training system 201 may include one or more devices that are not part of the cloud computing system 202, such as device 300 of FIG. 3, which may include a stand-alone server or another type of computing device. The training system 201 may perform one or more operations and/or processes described in more detail elsewhere herein.

The network 220 includes one or more wired and/or wireless networks. For example, the network 220 may include a cellular network, a public land mobile network (PLMN), a local area network (LAN), a wide area network (WAN), a private network, the Internet, and/or the like, and/or a combination of these or other types of networks. The network 220 enables communication among the devices of the environment 200.

The data structure 230 may include one or more devices capable of receiving, generating, storing, processing, and/or providing information, as described elsewhere herein. The data structure 230 may include a communication device and/or a computing device. For example, the data structure 230 may include a database, a server, a database server, an application server, a client server, a web server, a host server, a proxy server, a virtual server (e.g., executing on computing hardware), a server in a cloud computing system, a device that includes computing hardware used in a cloud computing environment, or a similar type of device. The data structure 230 may communicate with one or more other devices of the environment 200, as described elsewhere herein.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of the environment 200 may perform one or more functions described as being performed by another set of devices of the environment 200.

Figure 3:
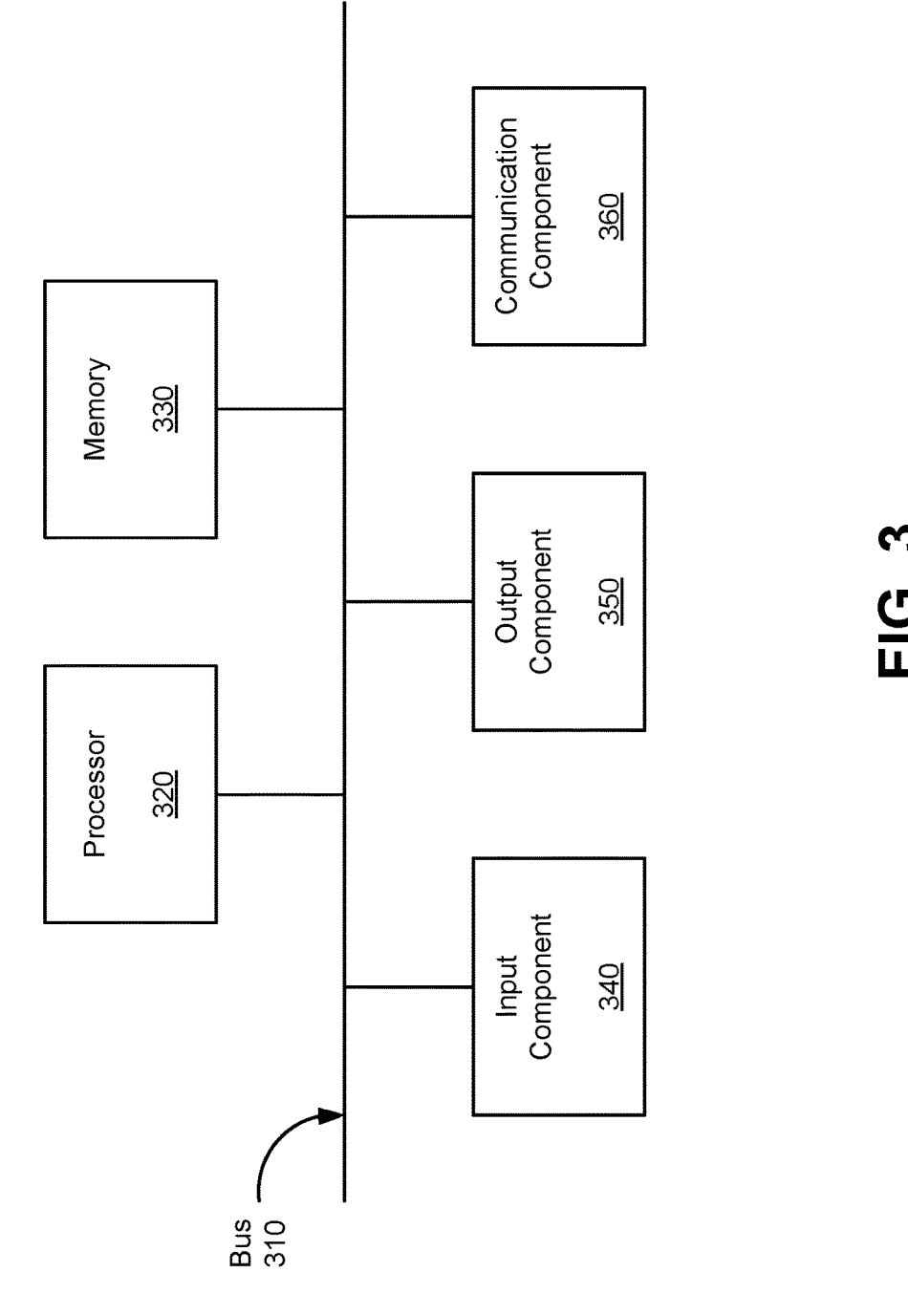
FIG. 3 is a diagram of example components of one or more devices of FIG. 2.

FIG. 3 is a diagram of example components of a device 300, which may correspond to the training system 201 and/or the data structure 230. In some implementations, the training system 201 and/or the data structure 230 may include one or more devices 300 and/or one or more components of the device 300. As shown in FIG. 3, the device 300 may include a bus 310, a processor 320, a memory 330, an input component 340, an output component 350, and a communication component 360.

The bus 310 includes a component that enables wired and/or wireless communication among the components of device 300. The processor 320 includes a central processing unit, a graphics processing unit, a microprocessor, a controller, a microcontroller, a digital signal processor, a field-programmable gate array, an application-specific integrated circuit, and/or another type of processing component. The processor 320 is implemented in hardware, firmware, or a combination of hardware and software. In some implementations, the processor 320 includes one or more processors capable of being programmed to perform a function. The memory 330 includes a random-access memory, a read only memory, and/or another type of memory (e.g., a flash memory, a magnetic memory, and/or an optical memory).

The input component 340 enables the device 300 to receive input, such as user input and/or sensed inputs. For example, the input component 340 may include a touch screen, a keyboard, a keypad, a mouse, a button, a microphone, a switch, a sensor, a global positioning system component, an accelerometer, a gyroscope, an actuator, and/or the like. The output component 350 enables the device 300 to provide output, such as via a display, a speaker, and/or one or more light-emitting diodes. The communication component 360 enables the device 300 to communicate with other devices, such as via a wired connection and/or a wireless connection. For example, the communication component 360 may include a receiver, a transmitter, a transceiver, a modem, a network interface card, an antenna, and/or the like.

The device 300 may perform one or more processes described herein. For example, a non-transitory computer-readable medium (e.g., the memory 330) may store a set of instructions (e.g., one or more instructions, code, software code, program code, and/or the like) for execution by the processor 320. The processor 320 may execute the set of instructions to perform one or more processes described herein. In some implementations, execution of the set of instructions, by one or more processors 320, causes the one or more processors 320 and/or the device 300 to perform one or more processes described herein. In some implementations, hardwired circuitry may be used instead of or in combination with the instructions to perform one or more processes described herein. Thus, implementations described herein are not limited to any specific combination of hardware circuitry and software.

The number and arrangement of components shown in FIG. 3 are provided as an example. The device 300 may include additional components, fewer components, different components, or differently arranged components than those shown in FIG. 3. Additionally, or alternatively, a set of components (e.g., one or more components) of the device 300 may perform one or more functions described as being performed by another set of components of the device 300.

Figure 4:
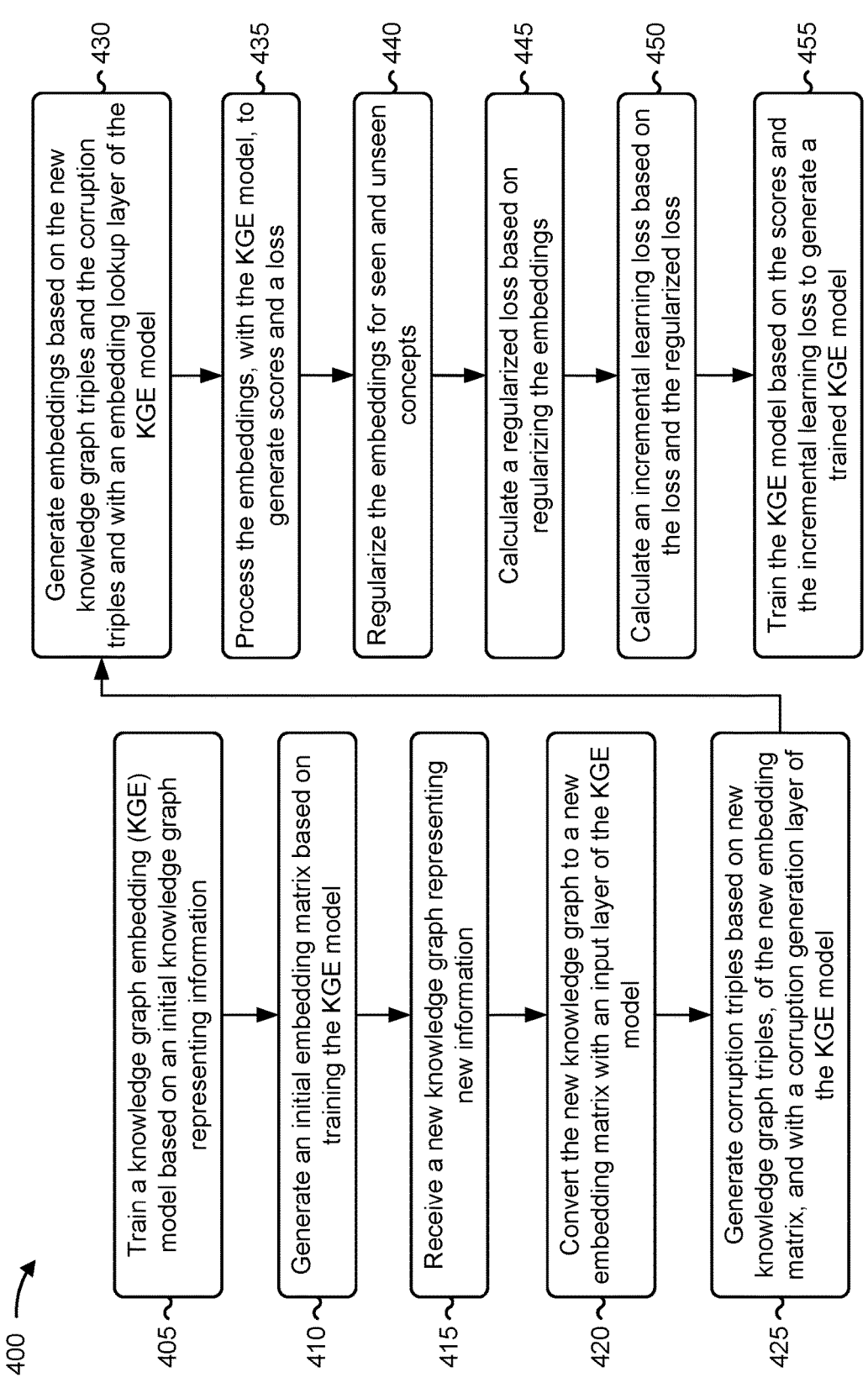
FIG. 4 is a flowchart of an example process for incrementally training a KGE model from biomedical knowledge graphs.

FIG. 4 is a flowchart of an example process 400 for incrementally training a KGE model from biomedical knowledge graphs. In some implementations, one or more process blocks of FIG. 4 may be performed by a device (e.g., the training system 201). In some implementations, one or more process blocks of FIG. 4 may be performed by another device or a group of devices separate from or including the device. Additionally, or alternatively, one or more process blocks of FIG. 4 may be performed by one or more components of the device 300, such as the processor 320, the memory 330, the input component 340, the output component 350, and/or the communication component 360.

As shown in FIG. 4, process 400 may include training a KGE model based on an initial knowledge graph representing information (block 405). For example, the device may train a KGE model based on an initial knowledge graph representing information, as described above.

As further shown in FIG. 4, process 400 may include generating an initial embedding matrix based on training the KGE model (block 410). For example, the device may generate an initial embedding matrix based on training the KGE model, as described above.

As further shown in FIG. 4, process 400 may include receiving a new knowledge graph representing new information (block 415). For example, the device may receive a new knowledge graph representing new information, as described above.

As further shown in FIG. 4, process 400 may include converting the new knowledge graph to a new embedding matrix with an input layer of the KGE model (block 420). For example, the device may convert the new knowledge graph to a new embedding matrix with an input layer of the KGE model, as described above.

As further shown in FIG. 4, process 400 may include generating corruption triples based on new knowledge graph triples, of the new embedding matrix, and with a corruption generation layer of the KGE model (block 425). For example, the device may generate corruption triples based on new knowledge graph triples and with a corruption generation layer of the KGE model, as described above. In some implementations, generating the corruption triples based on the new knowledge graph triples comprises generating the corruption triples by randomly replacing subjects or objects of the new knowledge graph triples with random entities from the new knowledge graph.

As further shown in FIG. 4, process 400 may include generating embeddings based on the new knowledge graph triples and the corruption triples and with an embedding lookup layer of the KGE model (block 430). For example, the device may generate embeddings based on the new knowledge graph triples and the corruption triples and with an embedding lookup layer of the KGE model, as described above.

As further shown in FIG. 4, process 400 may include processing the embeddings, with the KGE model, to generate scores and a loss (block 435). For example, the device may process the embeddings, with the KGE model, to generate scores and a loss, as described above. In some implementations, processing the embeddings, with the KGE model, to generate the scores includes processing the embeddings, with a scoring function, to calculate the scores, wherein the scoring function includes one or more of a TransE scoring function, a DistMult scoring function, a ComplEx scoring function, or a HoIE scoring function.

As further shown in FIG. 4, process 400 may include regularizing the embeddings for seen and unseen concepts (block 440). For example, the device may regularize the embeddings for seen and unseen concepts, as described above. In some implementations, regularizing the embeddings and the loss for seen and unseen concepts includes applying a first weight to the seen concepts, applying a second weight to the unseen concepts, and regularizing the embeddings and calculating the regularized loss based on applying the first weight to the seen concepts and applying the second weight to the unseen concepts.

As further shown in FIG. 4, process 400 may include calculating a regularized loss based on regularizing the embeddings (block 445). For example, the device may calculate a regularized loss based on regularizing the embeddings, as described above.

As further shown in FIG. 4, process 400 may include calculating an incremental learning loss based on the loss and the regularized loss (block 450). For example, the device may calculate an incremental learning loss based on the loss and the regularized loss, as described above.

As further shown in FIG. 4, process 400 may include training the KGE model based on the scores and the incremental learning loss to generate a trained KGE model (block 455). For example, the device may train the KGE model based on the scores and the incremental learning loss to generate a trained KGE model, as described above. In some implementations, training the KGE model based on the scores and the incremental learning loss to generate the trained KGE model includes minimizing the incremental learning loss based on the scores, and generating the trained KGE model based on minimizing the incremental learning loss.

In some implementations, process 400 includes merging the initial embedding matrix and the new embedding matrix to generate a final embedding matrix for the trained KGE model. In some implementations, process 400 includes converting the initial knowledge graph to an initial embedding matrix with the input layer of the KGE model; generating initial corruption data based on initial knowledge graph triples and with the corruption generation layer of the KGE model; generating initial embeddings based on the initial knowledge graph triples and initial corruption triples and with an embedding lookup layer of the KGE model; and processing the initial embeddings, with the KGE model, to compute a score and a loss and to generate a trained KGE model where the initial embeddings are trained based on the initial knowledge graph.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

The foregoing disclosure provides illustration and description but is not intended to be exhaustive or to limit the implementations to the precise form disclosed. Modifications may be made in light of the above disclosure or may be acquired from practice of the implementations.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, and/or the like, depending on the context.

Although particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

In the preceding specification, various example embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. A method, comprising:
   training, by a device, a knowledge graph embedding (KGE) model based on an initial knowledge graph representing information;
   generating, by the device, an initial embedding matrix based on training the KGE model, wherein the KGE model includes an input layer, a corruption generation layer, an embedding lookup layer, a scoring layer and a loss layer;
   receiving, by the device, a new knowledge graph representing new information, with the input layer of the KGE model;
   converting, by the device, the new knowledge graph to a new embedding matrix comprising new knowledge graph triples corresponding to the new knowledge graph, with the input layer of the KGE model;
   generating, by the device, corruption triples based on the new knowledge graph triples, of the new embedding matrix, and with the corruption generation layer of the KGE model;
   generating, by the device, embeddings based on the new knowledge graph triples and the corruption triples and with the embedding lookup layer of the KGE model;

processing, by the device, the embeddings of the embedding look up layer, with the KGE model, to generate scores with the scoring layer and a loss with the loss layer, wherein processing the embeddings of the embedding look up layer comprises:
      applying, by the device, a plausibility score to each of the new knowledge graph triples, and the corresponding corruption triples, with the scoring layer of the KGE model; and
      determining, by the device, the loss based on the plausibility scores, with the loss layer of the KGE model;
   regularizing, by the device, the embeddings for seen and unseen concepts;
   calculating providing, by the device, a regularized loss based on regularizing the embeddings;
   providing, by the device, an incremental learning loss based on the loss of the loss layer and the regularized loss; and
   training, by the device, the KGE model based on the scores of the scoring layer and the incremental learning loss by incrementally learning embeddings of the unseen concepts, and updating embeddings of the seen concepts to generate a trained KGE model.

2. The method of claim 1, further comprising:
   merging the initial embedding matrix and the new embedding matrix to generate a final embedding matrix for the trained KGE model.

3. The method of claim 1, further comprising:
   converting the initial knowledge graph to the initial embedding matrix with the input layer of the KGE model;
   generating initial corruption data based on initial knowledge graph triples and with the corruption generation layer of the KGE model;
   generating initial embeddings based on the initial knowledge graph triples and initial corruption triples and with an embedding lookup layer of the KGE model; and
   processing the initial embeddings, with the KGE model, to compute a score and a loss and to generate a trained KGE model where the initial embeddings are trained based on the initial knowledge graph.

4. The method of claim 1, wherein generating the corruption triples based on the new knowledge graph triples comprises:
   generating the corruption triples by randomly replacing subjects or objects of the new knowledge graph triples with random entities from the new knowledge graph.

5. The method of claim 1, wherein processing the embeddings, with the KGE model, to generate the scores comprises:
   processing the embeddings, with a scoring function, to calculate the scores, wherein the scoring function includes one or more of:
      a TransE scoring function,
      a DistMult scoring function,
      a ComplEx scoring function, or
      a HolE scoring function.

6. The method of claim 1, wherein training the KGE model based on the scores and the incremental learning loss to generate the trained KGE model comprises:
   minimizing the incremental learning loss based on the scores; and
   generating the trained KGE model based on minimizing the incremental learning loss.

7. The method of claim 1, wherein regularizing the embeddings and the loss for seen and unseen concepts comprises:

applying a first weight to the seen concepts;

applying a second weight to the unseen concepts; and regularizing the embeddings and calculating the regularized loss based on applying the first weight to the seen concepts and applying the second weight to the unseen concepts.

8. A device, comprising:

one or more memories; and one or more processors, coupled to the one or more memories, configured to:

train a knowledge graph embedding (KGE) model based on an initial knowledge graph representing information;

generate an initial embedding matrix based on training the KGE model, wherein the KGE model includes an input layer, a corruption generation layer, an embedding lookup layer, a scoring layer and a loss layer;

receive a new knowledge graph representing new information, with the input layer of the KGE model;

convert the new knowledge graph to a new embedding matrix with the input layer of the KGE model, wherein the new embedding matrix comprising new knowledge triples corresponding to the new knowledge graph;

generate corruption triples based on the new knowledge graph triples, of the new embedding matrix, and with the corruption generation layer of the KGE model;

generate embeddings based on the new knowledge graph triples and the corruption triples and with the embedding lookup layer of the KGE model process the embeddings, with the KGE model, to generate scores with the scoring layer and a loss with the loss layer, wherein to process the embeddings the one or more processors are configured to:

apply a plausibility score to each of the new knowledge graph triples, and the corresponding corruption triples, with the scoring layer of the KGE model; and determine the loss based on the plausibility scores, with the loss layer of the KGE model;

regularize the embeddings of the embedding lookup layer for seen and unseen concepts;

provide a regularized loss based on regularizing the embeddings;

provide an incremental learning loss based on the loss of the loss layer and the regularized loss; and train the KGE model based on the scores of the scoring layer and the incremental learning loss by incrementally training embeddings of unseen concepts, and updating embeddings of the seen concepts to generate a trained KGE model.

9. The device of claim 8, wherein the one or more processors are further configured to:

merge the initial embedding matrix and the new embedding matrix to generate a final embedding matrix for the trained KGE model.

10. The device of claim 8, wherein the one or more processors are further configured to:

convert the initial knowledge graph to the initial embedding matrix with the input layer of the KGE model;

generate initial corruption data based on initial knowledge graph triples and with the corruption generation layer of the KGE model;

generate initial embeddings based on the initial knowledge graph triples and initial corruption triples and with an embedding lookup layer of the KGE model; and process the initial embeddings, with the KGE model, to compute a score and a loss and to generate a trained KGE model where the initial embeddings are trained based on the initial knowledge graph.

11. The device of claim 8, wherein the one or more processors, to generate the corruption triples based on the new knowledge graph triples, are configured to:

generate the corruption triples by randomly replacing subjects or objects of the new knowledge graph triples with random entities from the new knowledge graph.

12. The device of claim 8, wherein the one or more processors, to process the embeddings, with the KGE model, to generate the scores, are configured to:

process the embeddings, with a scoring function, to calculate the scores, wherein the scoring function includes one or more of:

a TransE scoring function, a DistMult scoring function, a ComplEx scoring function, or a HolE scoring function.

13. The device of claim 8, wherein the one or more processors, to train the KGE model based on the scores and the incremental learning loss to generate the trained KGE model, are configured to:

minimize the incremental learning loss based on the scores; and generate the trained KGE model based on minimizing the incremental learning loss.

14. The device of claim 8, wherein the one or more processors, to regularize the embeddings and the loss for seen and unseen concepts, are configured to:

apply a first weight to the seen concepts;

apply a second weight to the unseen concepts; and regularize the embeddings and calculating the regularized loss based on applying the first weight to the seen concepts and applying the second weight to the unseen concepts.

15. A non-transitory computer-readable medium storing a set of instructions, the set of instructions comprising:

one or more instructions that, when executed by one or more processors of a device, cause the device to:

train a knowledge graph embedding (KGE) model based on an initial knowledge graph representing information;

generate an initial embedding matrix based on training the KGE model, wherein the KGE model includes an input layer, a corruption generation layer, an embedding lookup layer, a scoring layer and a loss layer;

receive a new knowledge graph representing new information, with the input layer of the KGE model;

convert the new knowledge graph to a new embedding matrix with an input layer of the KGE model, wherein the new embedding matrix comprising new knowledge triples corresponding to a new knowledge graph;

generate corruption triples based on the new knowledge graph triples, of the new embedding matrix, and with the corruption generation layer of the KGE model;

generate embeddings based on the new knowledge graph triples and corruption triples and with the embedding lookup layer of the KGE model;

process the embeddings, with the KGE model, to generate scores with the scoring layer and a loss with the loss layer, wherein to process the embeddings the one or more processors are configured to:

apply a plausibility score to each of the new knowledge graph triples, and the corresponding corruption triples, with the scoring layer of the KGE model; and determine the loss based on the plausibility scores, with the loss layer of the KGE model;

regularize the embeddings of the embedding lookup layer for seen and unseen concepts;

provide a regularized loss based on regularizing the embeddings;

provide an incremental learning loss based on the loss of the loss layer and the regularized loss; and train the KGE model based on the scores of the scoring layer and the incremental learning loss by incrementally training embeddings of unseen concepts, and updating embeddings of the seen concepts to generate a trained KGE model.

16. The non-transitory computer-readable medium of claim 15, wherein the one or more instructions further cause the device to:

merge the initial embedding matrix and the new embedding matrix to generate a final embedding matrix for the trained KGE model.

17. The non-transitory computer-readable medium of claim 15, wherein the one or more instructions further cause the device to:

convert the initial knowledge graph to the initial embedding matrix with the input layer of the KGE model;

generate initial corruption data based on initial knowledge graph triples and with the corruption generation layer of the KGE model;

generate initial embeddings based on the initial knowledge graph triples and initial corruption triples and with an embedding lookup layer of the KGE model; and process the initial embeddings, with the KGE model, to compute a score and a loss and to generate a trained KGE model where the initial embeddings are trained based on the initial knowledge graph.

18. The non-transitory computer-readable medium of claim 15, wherein the one or more instructions, that cause the device to generate the corruption triples based on the new knowledge graph triples, cause the device to:

generate the corruption triples by randomly replacing subjects or objects of the new knowledge graph triples with random entities from the new knowledge graph.

19. The non-transitory computer-readable medium of claim 15, wherein the one or more instructions, that cause the device to process the embeddings, with the KGE model, to generate the scores, cause the device to:

process the embeddings, with a scoring function, to calculate the scores, wherein the scoring function includes one or more of:

a TransE scoring function, a DistMult scoring function, a ComplEx scoring function, or a HolE scoring function.

20. The non-transitory computer-readable medium of claim 15, wherein the one or more instructions, that cause the device to train the KGE model based on the scores and the incremental learning loss to generate the trained KGE model, cause the device to:

minimize the incremental learning loss based on the scores; and generate the trained KGE model based on minimizing the incremental learning loss.

\* \* \* \* \*